United States Patent [19]

Kawabe et al.

[11] Patent Number: 5,763,652
[45] Date of Patent: Jun. 9, 1998

[54] PROCESS FOR PRODUCING A CARBOXYLIC ACID

[75] Inventors: Masato Kawabe; Kenichi Yamamoto, both of Himeji; Kazuyuki Matsuoka, Kitakatsuragi-gun, all of Japan

[73] Assignee: Daicel Chemical Industries, Ltd., Osaka, Japan

[21] Appl. No.: 611,877

[22] Filed: Mar. 6, 1996

[30] Foreign Application Priority Data

Mar. 8, 1995 [JP] Japan ................................. 7-078211
Jun. 22, 1995 [JP] Japan ................................. 7-181075

[51] Int. Cl.$^6$ .......................... C07C 51/62; C07C 51/367; C07C 51/08; C07C 51/06
[52] U.S. Cl. ..................... 562/512; 423/356; 423/470; 423/396; 423/302; 423/549
[58] Field of Search ..................... 562/526, 512; 423/356

[56] References Cited

U.S. PATENT DOCUMENTS

| | | | |
|---|---|---|---|
| 3,920,670 | 11/1975 | Norton | 260/295.5 R |
| 3,968,152 | 7/1976 | Sze et al. | 260/515 P |
| 4,304,934 | 12/1981 | Bartels-Keith et al. | 564/1 |
| 4,950,788 | 8/1990 | Farrar et al. | 562/598 |
| 5,210,309 | 5/1993 | Newkome et al. | 564/495 |

FOREIGN PATENT DOCUMENTS

| | | |
|---|---|---|
| 0438369 | 7/1991 | European Pat. Off. . |
| 0658371 | 6/1995 | European Pat. Off. . |
| 1260755 | 2/1969 | United Kingdom . |
| 1472530 | 6/1974 | United Kingdom . |

*Primary Examiner*—Johann Richter
*Assistant Examiner*—Laura Cross Lutz
*Attorney, Agent, or Firm*—Birch, Stewart, Kolasch & Birch, LLP

[57] ABSTRACT

A nitrile compound or an amide compound is hydrolyzed in the presence of an inorganic acid or other acidic catalyst or an alkali metal hydroxide or other basic catalyst, and the by-produced ammonium salt of the acidic catalyst or the produced salt of a carboxylic acid and a base is electrodialysed to form an acid and ammonia or aqueous ammonia, or to form a base and ammonia. The obtained acid or base may be recycled as a catalyst for the hydrolysis of the nitrile compound or amide compound, and the obtained ammonia is reutilized as a nitrogen source for the nitrile compound or amide compound. Such amide compound may be produced by hydration of a nitrite compound in the presence of a manganese oxide.

20 Claims, 2 Drawing Sheets

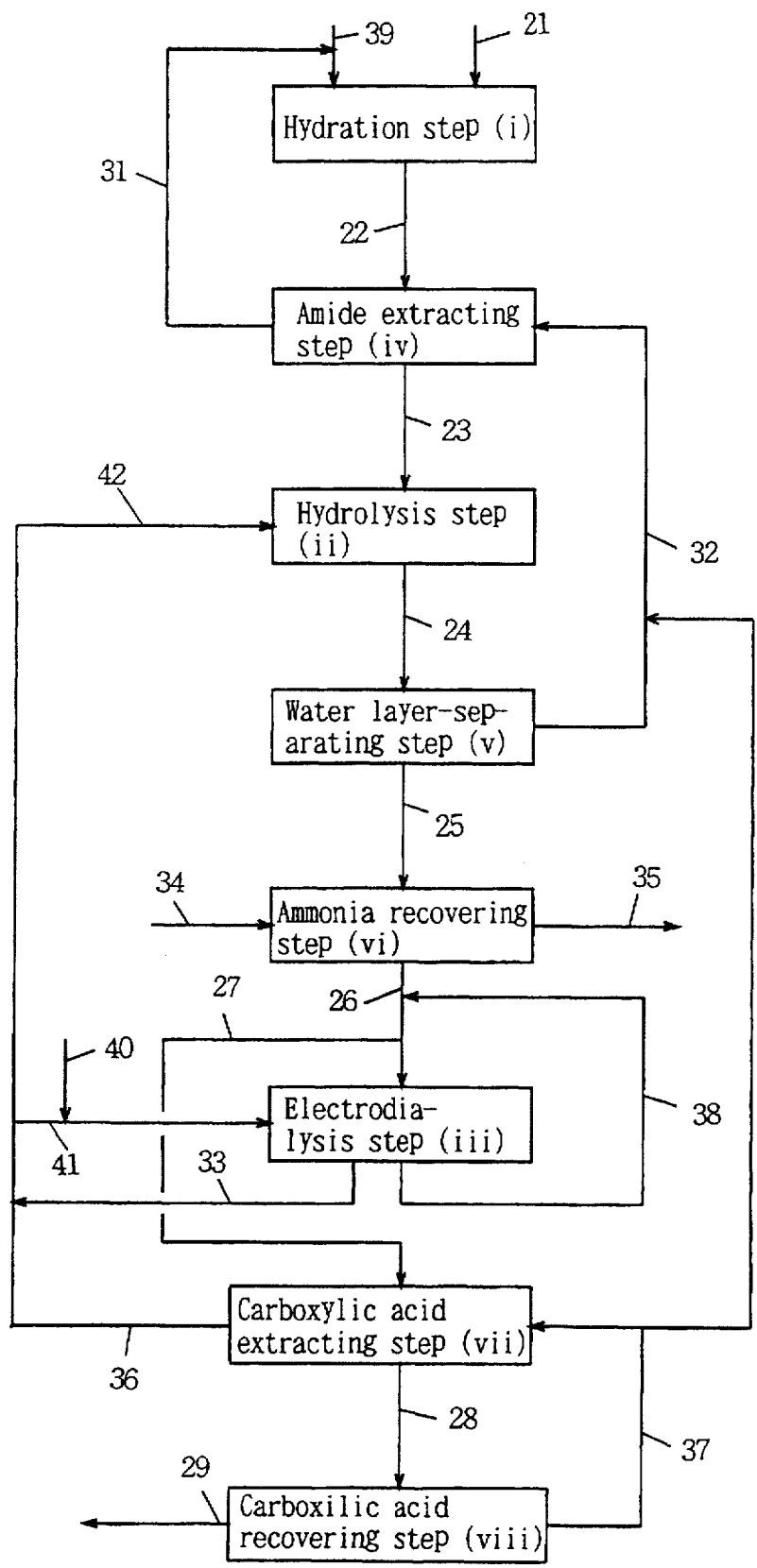

PROCESS FOR PRODUCING A CARBOXYLIC ACID

FIELD OF THE INVENTION

This invention relates to a process for producing a carboxylic acid from a nitrile compound or an amide compound. Such carboxylic acid is a remarkably important compound in the field of organic synthesis and is produced as an intermediate or a product.

BACKGROUND OF THE INVENTION

When a carboxylic acid is produced by hydrolyzing a nitrile compound or an amide compound, a concentrated sulfuric acid or other inorganic acid is usually used as a hydrolyzing catalyst. In this method, a nitrile compound is allowed to react with sulfuric acid so that an equivalent amount of ammonium hydrogensulfate relative to an objected carboxylic acid is by-produced as shown in the following reaction scheme (a).

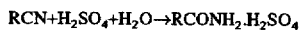

 (a)

The by-produced ammonium hydrogensulfate is discharged into a river or other environment as an industrial waste water. This waste water, however, causes an environmental destruction problem. Further, useful ammonia and sulfuric acid which are discharged or discarded without recovering, so that a production cost is increased and resources are not utilized effectively.

On the other hand, efforts have been made to develop treatment processes for the by-produced ammonium hydrogensulfate and production processes which do not give by-produced ammonium hydrogensulfate. By way of illustration, a process which comprises decomposing ammonium hydrogensulfate by heat-decomposition into nitrogen, $SO_2$ and water, oxidizing the produced $SO_2$ to give sulfuric acid, recovering the product sulfuric acid and recycling the same as a hydrolyzing catalyst for a nitrile compound as illustrated in the following scheme (b).

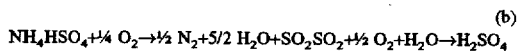 (b)

According to this process, the sulfur component of ammonium hydrogensulfate can be reutilized as sulfuric acid. However, (i) ammonia derived from ammonium hydrogensulfate can not be recovered since nitrogen gas is produced by heat-decomposition of ammonium hydrogen-sulfate. Further, (ii) the sulfuric acid gas is treated at a high temperature so that corrosion of an apparatus is remarkably enhanced and thus the apparatus needs to be renewed in a short period. Moreover, (iii) recovery and recycling of the sulfur component as sulfuric acid require a large quantity of steps such as a heat-decomposition step of ammonium hydrogensulfate, an isolation step of components produced by the heat-decomposition, an oxidizing step of $SO_2$ and an isolation step of sulfuric acid, and hence cause remarkably high plant and equipment cost. Accordingly, the abovementioned process is employed in a production plant for a carboxylic acid in a fairly large scale, but it is poorly applicable to general purpose and does not insure efficient production of a carboxylic acid at low cost. By the same token, similar problems exist in a case when a basic catalyst is used as a hydrolyzing catalyst.

SUMMARY OF THE INVENTION

Accordingly, it is an object of the present invention to provide a process for producing a carboxylic acid which ensures effective utilization of a by-produced salt of a catalytic component.

It is another object of the present invention to provide a process for forming a catalytic component (an acidic catalyst or a basic catalyst) in a simple and easy manner and ammonia or an aqueous ammonia with ease and efficiency and hence can effectively be utilized for production of a carboxylic acid.

A yet another object of the present invention is to provide a process for producing a carboxylic acid which does not produce ammonium hydrogensulfate or other by-products.

It is a further object of the present invention to provide a production process of a carboxylic acid which provides recovery of useful ammonia and catalyst in a simple and easy manner.

A still further object of the present invention is to provide a process for producing a carboxylic acid which insures effective utilization of ammonia and a catalytic component.

It is a yet another object of the invention to provide a production process of a carboxylic acid by which the catalytic component and ammonia can be reutilized with a high efficiency and can largely be applied to general purpose.

The present inventors made intensive investigations to accomplish the above objects, and found that a utilization of electrodialysis results in efficient decomposition of a by-produced salt of a catalytic component (an ammonium salt of an acidic catalyst or a salt formed with a carboxylic acid and a basic catalyst) so that the produced catalytic component and ammonia or an aqueous ammonia can effectively reutilized in a production process of a carboxylic acid from a nitrile compound or an amide compound. Further they found that a combination use of a hydration reaction of a nitrile compound with the use of a manganese oxide catalyst, a hydrolysis reaction using a base as a catalyst and electrodialysis results in production of a carboxylic acid without forming ammonium hydrogensulfate and other by-products. The present invention has been accomplished on the basis of the above findings.

Thus, the process of the present invention comprises (1) a step of hydrolyzing a nitrile compound or an amide compound (a) in the presence of an acidic catalyst to form a carboxylic acid and an ammonium salt of the acidic catalyst, or (b) in the presence of a basic catalyst to form a salt of a carboxylic acid and a base, and ammonia or aqueous ammonia, and (2a) a step of electrodialysing the by-produced ammonium salt of the acidic catalyst to form an acid and ammonia or aqueous ammonia, or (2b) a step of electrodialysing the produced salt of the carboxylic acid and the base to form the carboxylic acid and the base.

The acid or base produced in the electrodialysis may be reutilized as a catalyst for the hydrolysis step of the nitrile compound or the amide compound, and/or the ammonia or aqueous ammonia produced by the hydrolysis or electrodialysis may be recycled as a nitrogen source for the nitrile compound or the amide compound (processes A and B). In the present process, a nitrile compound may be hydrated in the presence of a manganese catalyst to form a corresponding amide compound, and the obtained amide compound may be subjected to the hydrolysis step (process C).

The electrodialysis can be effected by using an ion exchange membrane comprising a bipolar membrane and at least one membrane selected from a cation exchange membrane and an anion exchange membrane. The nitrile compound includes, for example, cyanhydrin compounds and the like. The base may have a pKa value of about 6 or more, and as the base, an alkali metal hydroxide can be employed, for instance. The process (C) may further comprises a base recycle step and ammonia recycle step (feeding step) as mentioned in the processes A and B, an amide compound extracting process of extracting a reaction mixture of the hydration step (i) and feeding the obtained organic layer containing the amide compound to the hydrolysis step (ii), a recycle step of extracting a mixture produced in the electrodialysis step (iii), separating an organic solvent from the obtained organic layer, and recycling the obtained organic solvent as an extractant for the amide extracting step or a carboxylic acid extracting step.

BRIEF DESCRIPTION OF THE DRAWINGS

FIG. 3 is a production flow chart showing an embodiment of the production process of the present invention.

DETAILED DESCRIPTION OF THE INVENTION

Figure 1:
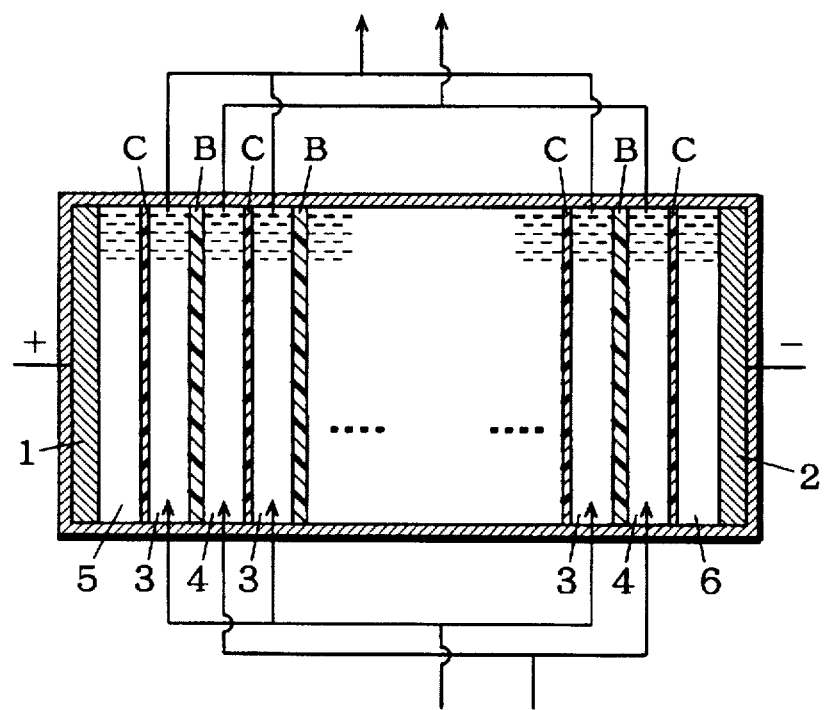
FIG. 1 is a schematic construction diagram illustrating an example of a two-chamber electrodialyser.

The present invention is now described with referring to the attached drawings where necessary.

The species of the nitrile compound and amide compound as used in the present invention are not strictly limited and can be selected from various compounds within a broad range. As typical example of the nitrile compound, there may be mentioned a compound shown by the formula RCN or RCOCN, and typical example of the amide compound can be shown by the formula $RCONH_2$, wherein R represents an aliphatic hydrocarbon group, an alicyclic hydrocarbon group, an aromatic hydrocarbon group or a heterocyclic group, and these groups may further have a substituent. Further, a polynitrile and a polyamide can also be employed as the nitrile compound and the amide compound respectively. That is, the above aliphatic hydrocarbon group, alicyclic hydrocarbon group, aromatic hydrocarbon group or heterocyclic group may be whichever of a monovalent group or a polyvalent group being divalent or more.

The aliphatic hydrocarbon group includes, for instance, saturated hydrocarbon groups or unsaturated hydrocarbon groups such as methyl, ethyl, propyl, isopropyl, butyl, isobutyl, s-butyl, t-butyl, pentyl, hexyl, octyl, decyl and other alkyl groups each having about 1 to 12 carbon atoms (preferably about 1 to 6 carbon atoms); vinyl, allyl, 1-propenyl, isopropenyl, 2-butenyl and other alkenyl groups each having about 2 to 12 carbon atoms; ethynyl, 2-propynyl and other alkynyl groups each having about 2 to 12 carbon atoms; alkylene groups each having about 2 to 12 carbon atoms and others.

Examples of the alicyclic hydrocarbon group include cyclopropyl, cyclobutyl, cyclopentyl, cyclohexyl, cyclooctyl and other cycloalkyl groups each having about 3 to 10 carbon atoms, and cycloalkylene groups corresponding to these cycloalkyl groups. As the aromatic hydrocarbon groups, there may be mentioned for example phenyl, naphthyl and other aryl groups each having about 6 to 14 carbon atoms, allylene groups corresponding to these aryl groups and so forth. The aralkyl group includes, for instance, benzyl, phenylethyl (phenethyl) and other aralkyl groups each having about 7 to 15 carbon atoms.

The heterocyclic group includes heterocyclic groups each having at least one atom, as a hetero atom, selected from the group consisting of a nitrogen atom, an oxygen atom and a sulfur atom, and may be whichever of an aromatic heterocyclic group, a non-aromatic heterocyclic group or a condensed heterocyclic group. As examples of the heterocyclic group, there may be mentioned furyl, thienyl, pyrrolyl, imidazolyl, pyrrolidinyl, pyridyl, pyrazinyl, pyrimidinyl, indolyl, pyridazinyl, piperidino, morpholino, morpholinyl, quinolyl and other groups.

These groups represented by R may further have a substituent. Examples of such substituent include halogen atoms, a hydroxyl group, alkyl groups (e.g. methyl, ethyl, propyl, isopropyl and other $C_{1-5}$ alkyl groups), aryl groups (e.g. phenyl, tolyl, xylyl, chlorophenyl, methoxyphenyl, naphthyl and other $C_{6-14}$ aryl groups), ether groups, alkoxy groups (e.g. methoxy, ethoxy and other $C_{1-5}$ alkoxy groups), aryloxy groups (e.g. phenoxy and other $C_{6-14}$ aryloxy groups), mercapto group, alkylthio groups (e.g. methylthio, ethylthio and other $C_{1-5}$ alkylthio groups), arylthio groups (e.g. phenylthio and other $C_{16-4}$ arylthio groups), carboxyl group, ester groups (e.g. methoxycarbonyl and other $C_{1-6}$ alkoxy-carbonyl groups); acetoxy and other $C_{2-12}$ acyloxy groups and so on), acyl groups (e.g. acetyl, benzoyl and other $C_{2-12}$ acyl groups), amino groups, mono- or di-substituted amino groups (e.g. methylamino, dimethylamino and other mono- or di-$C_{1-5}$ alkylamino groups), nitro group and the like. The number of such substituents to be substituted on the group represented by R may be about 1 to 4.

Examples of the aliphatic nitrile include nitriles each having a saturated or unsaturated aliphatic hydrocarbon group, such as saturated or unsaturated nitriles each having about 2 to 6 carbon atoms (for instance, acetonitrile, propionitrile, butyronitrile, isobutyronitrile, valeronitrile, isovaleronitrile, capronitrile and other saturated mononitriles; malononitrile, succinonitrile, glutaronitrile, adiponitrile and other saturated dinitriles; α-aminopropionitrile, α-aminomethylthiobutyronitrile, α-aminobutyronitrile, aminoacetonitrile and other α-aminonitriles; lactonitrile, hydroxyacetonitrile, α-hydroxyisobutyronitrile (acetocyanohydrin), α-hydroxy-γ-methylthiobutyronitrile (4-methylthio-2-hydroxybutyronitrile) and other α-hydroxynitriles; cyanoacetic acid and other nitriles each having a carboxyl group; amino-3-propionitrile and other β-aminonitriles, etc.), and unsaturated nitriles (e.g. acrylonitrile, methacrylonitrile, allyl cyanide, crotononitrile).

The aliphatic nitrile further includes compounds represented by RCOCN wherein R has the same meaning as above, such as pyruvonitrile (acetyl cyanide), cyanoacetone and others.

As the alicyclic nitrile, there may be mentioned for instance nitriles each having 4 to 10 carbon atoms such as cyclopentanecarbonitrile, cyclohexanecarbonitrile and the like.

Examples of the aromatic nitrile include benzonitrile, o-, m- and p-chlorobenzonitrile, o-, m- and p-fluorobenzonitrile, o-, m- and p-nitrobenzonitrile, p-aminobenzonitrile, 4-cyanophenol, o-, m- and p-tolunitrile, 2,4-dichlorobenzonitrile, 2,6-dichlorobenzonitrile, 2,6-difluorobenzonitrile, anisonitrile, α-naphthonitrile, β-naphthonitrile and other aromatic mononitriles; phthalonitrile, isophthalonitrile, terephthalonitrile and other aromatic dinitriles and so forth.

The aromatic nitrile also includes, for example, benzyl cyanide, cinnamoyl nitrile, phenylacetonitrile, mandelonitrile, p-hydroxyphenylacetonitrile, p-hydroxyphenylpropionitrile, p-methoxyphenylacetonitrile and other nitrites each having an aralkyl group.

As the heterocyclic nitrile, there may be mentioned, for instance, nitrile compounds each having a heterocyclic group containing 5- or 6-membered ring and having at least one atom selected from the group consisting of a nitrogen atom, an oxygen atom and a sulfur atom as a hetero atom, such as 2-thiophenecarbonitrile, 2-furonitrile, and other nitriles each having a sulfur atom or an oxygen atom as a hetero atom; 2-cyanopyridine, 3-cyanopyridine, 4-cyanopyridine, cyanopyrazine and other nitrites each containing a nitrogen atom as a hetero atom; 5-cyanoindole and other condensed heterocycles; cyanopiperidine, cyanopiperazine and other hydrogenated heterocyclic nitrites, condensed heterocyclic nitriles and so on.

Such heterocyclic nitrile also includes compounds represented by RCOCN, where R represents a heterocyclic group, such as nicotinonitrile, isonicotinonitrile and the like.

In more detail, the nitrile compound, in which the aliphatic hydrocarbon group, alicyclic hydrocarbon group, aromatic hydrocarbon group or heterocyclic group each represented by R has a substituent, includes for example amino-nitrile compounds, cyanohydrin compounds and so forth. As examples of the aminonitrile compound, there may be mentioned aminoacetonitrile, α-aminopropionitrile, α-aminobutyronitrile and other α-aminonitriles; 3-aminopropionitrile and other β-aminonitriles.

Examples of the cyanohydrin compound include α-cyanohydrin compounds, β-cyanohydrin compounds, γ-cyanohydrin compounds and others. Such cyanohydrin compound may contain, for instance, about 2 to 18, preferably about 3 to 12, and more preferably about 3 to 8 carbon atoms.

As the α-cyanohydrin compound, there may be mentioned a compound shown by the following formula (Ia)

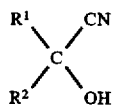

(Ia)

wherein $R^1$ and $R^2$ independently represent a hydrogen atom or a hydrocarbon group which may have a substituent, and $R^1$ and $R^2$ may form a ring together with the adjacent carbon atom, with a proviso that $R^1$ and $R^2$ are not concurrently hydrogen atoms.

Examples of the hydrocarbon group represented by $R^1$, $R^2$, and the substituent which the hydrocarbon group may have include the aliphatic hydrocarbon groups, alicyclic hydrocarbon group, aromatic hydrocarbon group, and the substituents which these groups may have, as exemplified in the explanation of the group R.

Preferred $R^1$ and $R^2$ include, as described in the explanation of R, the alkyl groups each having about 1 to 12 (preferably about 1 to 6) carbon atoms, the alkenyl groups each having about 2 to 12 carbon atoms, the alkynyl groups each having about 2 to 12 carbon atoms, the cycloalkyl groups each having about 3 to 10 carbon atoms, the aryl groups each having about 6 to 14 carbon atoms, and phenylmethyl, 2-phenylethyl, 1-phenylethyl, 3-phenylpropyl, 4-phenylbutyl group and other $C_{7-10}$ aralkyl groups.

As examples of the ring which is formed with $R^1$ and $R^2$ together with the adjacent carbon atom, there may be mentioned cyclopropyl, cyclobutyl, cyclopentyl, cyclohexyl, cycloheptyl, cyclooctyl ring and other cycloalkane rings each having about 3 to 8 carbon atoms.

Typical examples of the α-cyanohydrin compound include hydroxyacetonitrile, lactonitrile, acetone cyanohydrin, 2-hydroxybutanenitrile, 2-hydroxy-4-methylthiobutanenitrile, 2-hydroxy-2-methylbutanenitrile, 2-hydroxy-3-methylbutanenitrile, 2-hydroxy-3-butenenitrile, 2-hydroxypentanenitrile, 2-hydroxyhexanenitrile, 2-hydroxyoctanenitrile and other aliphatic α-cyanohydrins; 2-hydroxy-cyclohexaneacetonitrile, cyclopentanone cyanohydrin, cyclohexanone cyanohydrin and other alicyclic α-cyanohydrins; mandelonitrile, 2-hydroxy-3-phenylbutanenitrile and other aromatic α-cyanohydrins.

As the β-cyanohydrin compound, use can be made of 3-hydroxypropanenitrile, 3-hydroxybutanenitrile, 3-hydroxyhexanenitrile, 2-hydroxycyclohexanecarbonitrile or 3-hydroxy-3-phenylpropanenitrile, for example.

The γ-cyanohydrin compound includes, for instance, 4-hydroxybutanenitrile, 4-hydroxyhexanenitrile, 3-hydroxyhexanecarbonitrile, 4-hydroxy-4-phenylbutanenitrile and so on.

Since the electrodialysis step in the present invention may usually be conducted in the presence of water, the nitrile compound may preferably be a compound where a corresponding salt of a carboxylic acid is water-soluble. From this point of view, the nitrile compound may have, as the total carbon atoms, about 2 to 18, preferably about 2 to 12, and more preferably about 2 to 8 carbon atoms, typically speaking.

Preferred examples of the nitrile compound include cyanohydrin compounds, in particular, α-cyanohydrin compounds such as compounds shown by the formula (Ia) which are useful for production of a hydroxycarboxylic acid. More preferably, the nitrile compound includes for instance lactonitrile, acetone cyanohydrin, 2-hydroxy-4-methylthiobutanenitrile and other aliphatic α-cyanohydrins each having about 3 to 8 carbon atoms.

Incidentally, when the nitrile compound has a plurality of cyano groups, it may only have at least one amide group or carboxyl group converted from one cyano group, and when the amide group have plural amide groups, at least one amide group may only be converted to a carboxyl group.

Meanwhile, the nitrile compound as mentioned above can be obtained in a conventional manner. Taking an aliphatic nitrile as an example, it may be prepared by allowing a halogenated alkyl or dialkyl sulfate to react with potassium cyanide or other alkali cyanide. The aromatic nitrile can be produced by, for instance, a process comprising diazotizing an amine and allowing the resultant to react with copper (I) cyanide or other techniques.

In particular, the α-cyanohydrin compound among such nitrile compounds may be prepared by, for instance, a process which comprises allowing cyanide to react with an aldehyde or a ketone, a process which comprises allowing an adduct derived from an aldehyde or ketone and sodium hydrogensulfite to react with an alkali cyanide such as potassium cyanide or others. The β-cyanohydrin compound can be prepared by allowing an epoxide to react with hydrogen cyanide, for example.

As examples of the amide compound, there may be mentioned compounds corresponding to the above nitrile compounds, such as acetamide, propionamide, butyramide, isobutyramide, acrylamide, methacrylamide, lactoamide, pyruvoamide, α-hydroxyisobutyramide, 4-methylthio-2- hydroxyisobutyramide, phenylacetamide, mandelamide, p-hydroxyphenylacetamide, p-hydroxyphenylpropionamide, p-methoxyphenylacetamide, terephthalamide, nicotinamide, isonicotinamide and so forth.

The processes (A) and (B) of the present invention are now described in detail.

There is no limit as to the catalyst in the hydrolysis reaction as far as being utilizable in a hydrolysis of a nitrile compound or an amide compound, and a variety of acidic catalysts and basic catalysts can be employed.

Examples of the acidic catalyst include hydrochloric acid, nitric acid, phosphoric acid, sulfuric acid and other inorganic acids, trichloroacetic acid, trifluoroacetic acid, methanesulfonic acid and other organic acids. These acidic catalysts may be used singly or in combination. Preferred acidic catalyst includes mineral acids (e.g. sulfuric acid and other inorganic acids).

As the basic catalyst for hydrolysis of the amide compound, there may be mentioned for instance sodium hydroxide, potassium hydroxide and other hydroxides of alkali metals, sodium carbonate, potassium carbonate, sodium hydrogencarbonate, potassium hydrogencarbonate and other carbonates of alkali metals and so on. Such basic catalysts may also be employed independently or in combination. Preferred examples of the basic catalyst include hydroxides of alkali metals.

The present invention can be applied to (A) a method of a carboxylic acid by hydrolyzing a nitrile compound or an amide compound in the presence of an acidic acid. Taking a typical nitrile compound and amide compound as an example, the production reaction of a carboxylic acid can be represented by the following reaction scheme (1A) or (1B).

(i) Hydrolysis of a nitrile compound (hydration)

$$RCN + HA + 2\ H_2O \rightarrow RCOOH + NH_4A \quad (1A)$$

wherein HA represents an acidic catalyst, and R has the same meaning as above.

(ii) Hydrolysis of an amide compound (hydration)

$$RCONH_2 + HA + H_2O \rightarrow RCOOH + NH_4A \quad (1B)$$

wherein R and HA have the same meanings as above.

The amount of the acidic catalyst may suitably be selected from a range not inferring with the hydrolysis reaction, and is for example about 0.75 to 10 moles, preferably about 0.9 to 5 moles, more preferably about 1 to 3 moles and practically about 1 to 2.5 moles per mole of the nitrile compound or amide compound.

The amount of water in the hydrolysis reaction may only be an excess mole relative to the nitrile compound or amide compound, as apparent from the above reaction schemes. The relative proportion of the water to 1 mole of the nitrile compound is, for instance, about at least 1.5 mole or more (e.g. about 1.5 to 50 moles), preferably about 2 to 25 moles and more preferably about 2.2 to 10 moles. The water may practically be used in an excess amount (e.g. about 2.5 to 10 moles) relative to the nitrile compound. The amount of the water relative to 1 mole of the amide compound may be about at least 0.7 mole or more (e.g. about 0.8 to 50 moles), preferably about 1 to 25 moles, more preferably about 1.2 to 10 moles and practically about an excess mole (e.g. about 1.5 to 10 moles).

The reaction may be carried out in an inert solvent as necessary. Such inert solvent includes, for example, hexane, octane and other aliphatic hydrocarbons, cyclohexane and other alicyclic hydrocarbons, benzene, xylene, toluene and other aromatic hydrocarbons, dichloromethane, carbon tetrachloride and other halogenated hydrocarbons, methanol, ethanol, propanol, isopropanol, butanol and other alcohols, methyl acetate, ethyl acetate, isobutyl acetate and other esters, dimethyl ether, diethyl ether, dioxane, tetrahydrofuran and other ethers, acetone, methyl ethyl ketone, methyl isobutyl ketone and other ketones, aprotic solvents and so forth. These solvents may be employed singly or in combination.

The hydrolysis can be conducted in a suitable condition, such as at a temperature of about 30° to 200° C., preferably about 50° to 150° C. and more preferably about 60° to 120° C.

The by-produced ammonium salt of the acidic catalyst by-produced by the hydrolysis is subjected to electrodialysis to give an acid and ammonia (or aqueous ammonia). The reaction in the electrodialysis step can be illustrated by the following reaction scheme (reaction formula).

$$NH_4A + H_2O \rightarrow NH_4OH + HA$$

$$NH_4OH \rightarrow H_2O + NH_3$$

As apparent from the above reaction formula, for effective reutilization of by-products, the process may preferably comprise at least either one step of (1) a step of reutilizing an acid produced by the electrodialysis as a catalyst in the hydrolysis step of the nitrile compound or amide compound, and (2) a step of reutilizing ammonia or aqueous ammonia produced by the electrodialysis as a nitrogen source for the nitrile compound or amide compound. Preferred process comprises both of (1) the reutilizing step of the acid and (2) the reutilizing step of the ammonia (or aqueous ammonia). Further, the separated water may be subjected or supplied to the hydrolysis step of the nitrile compound or amide compound.

Incidentally, the nitrile compound may also be prepared by a conventional technique with the use of the ammonia as a nitrogen source, such as reaction of an aldehyde compound with ammonia, reaction of a carboxylic acid with ammonia or others. The amide compound can be prepared in a conventional manner using the ammonia as a nitrogen source, such as reaction of a carboxylic acid with ammonia. Further, the present invention may also be applied to (B) a process of producing a carboxylic acid by hydrolyzing the nitrile compound or amide compound in the presence of a basic catalyst. By taking a typical nitrile compound and amide compound as an example, the production reaction of a carboxylic acid can be shown by the following reaction formulas (2A) or (2B).

(iii) Hydrolysis of the nitrile compound:

$$RCN + MOH + 2\ H_2O \rightarrow RCOOM + NH_4OH \quad (2A)$$

wherein MOH represents a basic catalyst and R has the same meaning as above.

(iv) Hydrolysis of the amide compound:

$$RCONH_2 + MOH + H_2O \rightarrow RCOOM + NH_4OH \quad (2B)$$

wherein R and MOH have the same meanings as above.

The amount of the basic catalyst and the proportion of the water in the hydrolysis reaction in the presence of the basic catalyst are similar to those of the hydrolysis reaction with the use of the acidic catalyst, as apparently shown in the above schemes.

The salt of a carboxylic acid and a base is subjected to hydrolysis to form the carboxylic acid and the base. The reaction in the electrodialysis step may be represented by the following scheme (formula).

$$RCOOM+NH_4OH \rightarrow RCOOM+H_2O+NH_3\uparrow$$
$$RCOOM+H_2O \rightarrow RCOOH+MOH$$

The process (B) of the present invention comprises at least either one step of (1) a step of reutilizing a base produced by the electrodialysis as a catalyst in the hydrolysis step of the nitrile compound, and (2) a step of reutilizing ammonia or aqueous ammonia produced by the electrodialysis as a nitrogen source in a production process of the nitrile compound or amide compound. For the purpose of further utilizing the by-products in the hydrolysis reaction, it is preferable for the present process to comprise both steps of (1) the reutilizing step of the base and (2) the reutilizing step of ammonia (or aqueous ammonia).

The electrodialysis can be effected by a various techniques, for example by a process which comprises ion-dissociating an ammonium salt of the acidic catalyst or a salt of a carboxylic acid and the basic catalyst with the use of a membrane capable of ion transporting or ion exchanging while applying a voltage, and allowing the resultant cation or anion to selectively permeate the membrane for separation.

The species of the cation exchange membrane is not critically limited and use may be made of various membranes having cation exchanging capabilities, such as cation exchange membranes each having a cation exchange group including a sulfonic acid group, carboxyl group, a perfluoroalkylcarboxyl group, a phosphonic acid group, a sulfuric acid ester group, a phosphoric acid ester group, a carboxylic acid ester group, a perfluoroalkylcarboxylic acid ester group, sulfonamide group and others. A base material of the membrane may have a plural species of the cation exchange groups. Preferred examples of the cation exchange group include sulfonic acid group, carboxyl group and a perfluoroalkylcarboxyl group.

The species of the anion exchange membrane is also not particularly restricted, and use can be made of a variety of anion exchange membranes including anion exchange membranes each having a primary amino group, a secondary amino group, a tertiary amino group, a quaternary amino group (quaternary ammonium salt) and so on. A base material of such membrane may have plural species of anion exchange groups. Preferred anion exchange group includes a group of a quaternary ammonium salt.

As the base material having the ion exchange group, there may be mentioned various polymers such as polytetrafluoroethylene and other fluororesins, crosslinked polymers (e.g. a styrene-divinylbenzene series polymer, a vinyl-divinylbenzene series polymer, a styrene-butadiene series polymer, etc.), acrylic polymers, condensed polymers (e.g. an ethyleneimine-epichlorohydrin polymer or an epoxy polymer) and so forth. Further, according to the species of the ion exchange membrane, use can also be made of a polyethylene, a polypropylene, a poly(vinyl chloride), a polyester, a polyamide, a polyurethane and other thermoplastic resins, a phenolic resin, a vinyl ester resin and other thermosetting resins. The base material may be reinforced by a support such as a reinforcing fiber or a cloth.

Further, the ion exchange membrane used in the electrodialysis may be whichever of a homogeneous membrane,
a heterogeneous membrane, a fused membrane or an impregnated membrane, for instance. The ion exchange membrane may also be a composite membrane having an anion exchanging capability on one surface and a cation exchanging capability on the other surface of the membrane (a bipolar membrane), an amphoteric membrane having both of an anion exchange group and a cation exchange group, or others.

The electrodialysis corresponds, theoretically, to a hydrolysis of a salt described in the page 233 of "Ion Exchange Membrane" (edited by Yujiro KOSAKA and Hiroshi SHIMIZU, published by Kyoritsu Shuppan Co., Ltd., Japan), and there can be referred to such literature concerning a method for the electrodialysis techniques. By way of illustration, the electrodialysis may be effected by using a multichamber electrodialysis vessel (electrodialyser) in which a cation exchange membrane and an anion exchange membrane are disposed alternately and a voltage is applied to electrodes at both ends. For enhancing current efficiency, it is preferable to use an electrodialyser equipped with a bipolar membrane, and an ion exchange membrane comprising at least one membrane selected from a cation exchange membrane and an anion exchange membrane.

The species of the electrodialyser is not critical and a conventional two-chamber or three-chamber electrodialyser may preferably be employed. The two-chamber electrodialyser may be composed of plural of bipolar membranes which are disposed in such a manner that each anion exchange membrane side faces to an anode side and each cation exchange membrane side faces to a cathode side, and cation exchange membranes or anion exchange membranes each disposed between these bipolar membranes. Thus, by applying a voltage (potential) between the electrodes at both ends, a water molecule or a salt, which is penetrated into an interface of the anion exchange membrane portion and the cation exchange portion of the bipolar membrane, is decomposed or disintegrated to produce $H^+$ ion or a cation in the anion exchange membrane side, and $OH^-$ ion or an anion in the cation exchange membrane side of the bipolar membrane.

Figure 2:
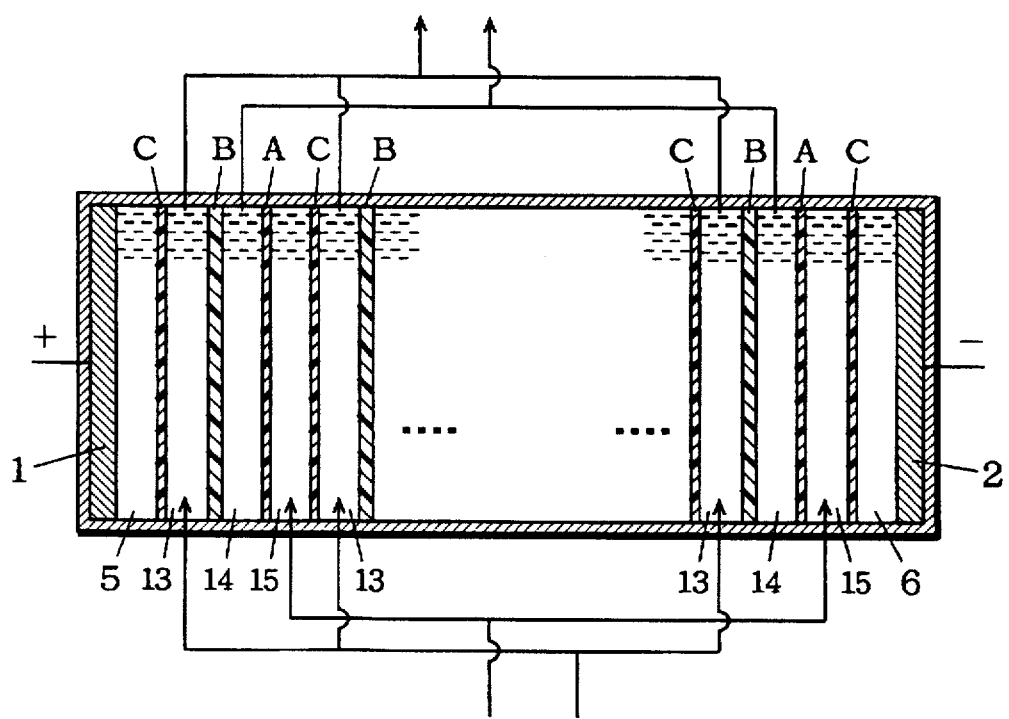
FIG. 2 is a schematic construction diagram illustrating an example of a three-chamber electrodialyser.

As shown in FIG. 1, a two-chamber electrodialyser using a bipolar membrane and a cation exchange membrane can for example be constructed by disposing plural of bipolar membranes B and plural of cation exchange membranes C alternately between an anode 1 and a cathode 2. A three-chamber electrodialyser as produced by using a bipolar membrane, a cation exchange membrane and an anion exchange membranes may be prepared by, for instance as illustrated in FIG. 2, disposing bipolar membranes B, anion exchange membranes A and cation exchange membranes C, in turns, between an anode 1 and a cathode 2.

In the electrodialyser, the cation exchange membrane is disposed as facing to an anion exchange membrane of the bipolar membrane, and the anion exchange membrane is disposed as facing to a cation exchange membrane of the bipolar membrane. Further, the two-chamber electrodialyser may usually be equipped with, in the direction from a cathode chamber 6 toward an anode chamber 5, a chamber (acid-base mixing chamber) 4 for accommodating a reaction mixture containing a salt (an ammonium salt of the acidic catalyst or a salt of a carboxylic acid and the basic catalyst), and a chamber (an acid chamber or an alkali chamber) 3 for accommodating a solution of the catalytic component (the acidic catalyst or basic catalyst). The three-chamber electrodialyzer may usually comprise, in the direction from a cathode chamber 6 toward an anode chamber 5, a chamber (a salt chamber) 15 for accommodating a reaction mixture containing the salt (an ammonium salt of the acidic catalyst or the salt of a carboxylic acid and the basic catalyst), an acid chamber 14 for accommodating an acid, and an alkali chamber 13 for accommodating an alkali (base).

The bipolar membrane can be obtained according to a conventional technology. As such technology, there may be mentioned for example a process which comprises laminating a cation exchange membrane and an anion exchange membrane each other with the use of a mixture of polyethylene-epichlorohydrin to cure and adhere the membranes [Japanese Patent Publication No. 3962/1957 (JP-B-32-3962)], a process which comprises pressing two membranes a paste mixture of a finely powdered cation exchange resin or anion exchange resin and a thermoplastic substance for adhesion [Japanese Patent Publication No. 14531/1960 (JP-B-35-14531)], a process which comprises applying a glue-like substance comprising vinylpyridine and an epoxy compound to the surface of a cation exchange membrane and irradiating a radiation (radioactive ray) to the resultant [Japanese Patent Publication No. 16633/1963 (JP-B-38-16633)], a process which comprises attaching a sulfonic acid-type polymeric electrolyte and an allylamine to the surface of an anion exchange membrane and irradiating an electrolytically dissociating radiation to the resultant for crosslinking [Japanese Patent Publication No. 4113/1976 (JP-B-51-4113)], a process which comprises precipitating or depositing, to a surface of an ion exchange membrane, a mixture of a dispersing system of an ion exchange resin having the opposed charge relative to the ion exchange membrane and a mother polymer [Japanese Patent Application Laid-open No. 37190/1978 (JP-A-53-37190)], a process which comprises holding a sheet-like substance obtained by impregnating-polymerization styrene and divinylbenzene to a polyethylene film, between a frame made of stainless steel or so forth, sulfonating one surface of the sheet, chloromethylating the other surface of the sheet, and aminating the resultant [U.S. Pat. No. 3,562,139], a process which comprises treating an interface of a cation exchange membrane and an anion exchange membrane with an inorganic compound and adhering the both membranes each other [Japanese Patent Application Laid-open No. 47235/1984 (JP-A-59-47235)].

The condition of the electrodialysis can be selected from a broad range as far as not sacrificing utilization efficiencies of the acidic catalyst or basic catalyst, and ammonia or aqueous ammonia, and the temperature is, for example about 0° to 100° C., preferably about 10° to 70° C. and more preferably about 20° to 50° C., and the electric current density is about 1 to 30 A/dm² and preferably about 3 to 20 A/dm², for instance.

According to the process of the present invention, a by-produced salt can be decomposed by electrodialysis and the produced acidic catalyst, basic catalyst or ammonia can be reutilized in the production step of a carboxylic acid. Therefore, the process is useful for producing a carboxylic acid with preventing environmental pollution. Still more, a carboxylic acid can be produced with the use of a simple construction and further with few steps of a combination of a conventional apparatus and an electrodialyser.

A reaction scheme of the present production process (C) is illustrated as follows, when the compound shown by RCN, wherein R has the same meaning as above is employed as a typical example of the nitrile compound.

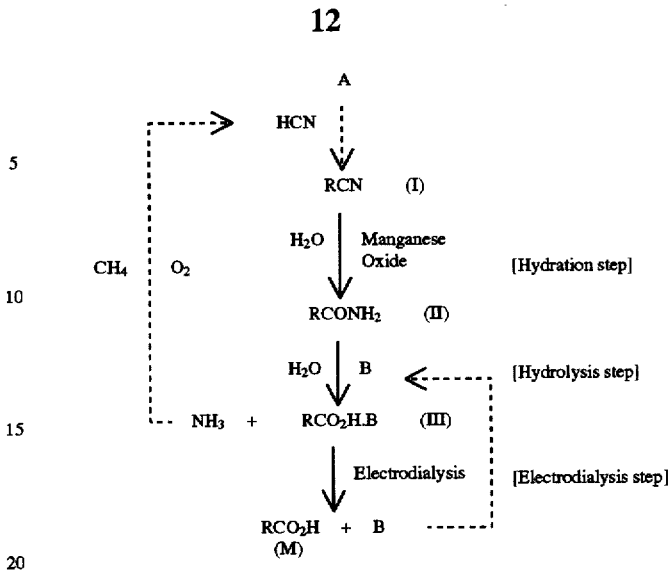

FIG. 3 is a production scheme (flow chart) illustrating an embodiment of the production process (C) of the present invention. The process (C) of the present invention is now illustrated with referring to FIG. 3.

Hydration step

In the hydration step, a nitrile compound shown by the formula RCN (I)

wherein R has the same meaning as above, is hydrated in the presence of a manganese oxide catalyst to form a corresponding amide compound (II). Since a manganese oxide is used in this process, this process does not by-produce a reaction product derived from the nitrile compound, which is different from a process with the use of sulfuric acid as a catalyst. Accordingly, it is not necessary to discharge a large quantity of by-products, and complicated steps for regeneration of the catalyst are not required.

According to an embodiment as illustrated in FIG. 3, in the hydration step (i), a reactor is respectively charged with a nitrile compound from a nitrile supply line 21, and water from a water supply line 39, and hydration reaction is carried out in the present of a manganese oxide catalyst. Meanwhile, a water-phase of an amide extracting step (iv) described hereafter may be supplied to the reactor through a water recycle line (water recycle line) 31.

The species of the manganese oxide used as the catalyst is not strictly limited and those having various valencies may be employed. Among them, a manganese dioxide can preferably be used. Such manganese dioxide is generally shown as $MnO_{1.7}$ to $MnO_2$, and as a crystal structure of the manganese dioxide, there may be mentioned an α-, β-, γ- or δ-structure, for instance. Typically preferred manganese oxide includes a manganese dioxide having a δ-structure.

The manganese dioxide with a δ-structure may be prepared by, for example, reducing a manganese compound with hepta (7) valent in a neutral to alkalescent condition at a reaction temperature of about 20° to 100° C. [see Z. Anorg. Allg. Chem., 309, p10–14 (1961)].

For the purpose of enhancing the reaction rate, selectivity of the objective substance and catalyst life (catalyst cycle) in the hydration step (i), a metallic simple substance or compound containing Group Ia elements (e.g. Na, K, etc.), Group IIa elements (e.g. Mg, Ca, Ba, etc.), Group IIb elements (e.g. Zn), Group IVa elements (e.g. Zr, etc.), Group IVb elements (e.g. Sn, etc.), Group Va elements (e.g. V, etc.) or others, each of which group is of the Periodic Table of Elements, may be used together with the manganese oxide.

The amount of water in the hydration step (i) is, for instance relative to 1 mole of the nitrile compound, not less than 0.5 mole (e.g. about 0.5 to 300 moles), and preferably not less than 1 mole (e.g. about 1 to 150 moles). For increasing the solubility of the nitrile compound and stimulating the reaction smoothly, a water-soluble organic solvent such as acetone and other ketones; methanol, ethanol and other alcohols; and dimethoxyethane, tetrahydrofuran, dioxane and other ethers may be added to the reaction system.

The reaction may usually conducted at a temperature of about 20° to 150° C., and preferably about 30° to 120° C. When the reaction temperature is lower than 20° C., the reaction time is apt to be prolonged, and when it exceeds 150° C., a side reaction such as dehydrogencyanide reaction is promoted so that a yield is liable to be sacrificed. The reaction pressure may be any of pressure as far as the reaction system can be maintained as a liquid phase at the reaction temperature, and for example is about 1 to 20 atm and preferably about 1 to 10 atm. The reaction may practically be carried out at an atmospheric pressure. The reaction time depends on a reaction manner, reaction temperature, species and/or amount of the manganese oxide catalyst or other factors, so as not to be described in a word, but generally is about 0.4 to 12 hours.

Regarding the reaction manner, the reaction can be conducted in whichever of a fixed bed method, fluidized bed method or other method, and by whichever of a batch system or flow system. The shape or configuration of the catalyst is not critical and the catalyst may be powdery, granular (particulate) or other form, and it may also be molded. The catalyst can also be used as a slurry catalyst.

Amide extracting step

A reaction mixture containing an amide compound (II) produced in the hydration step may be subjected to the amide extracting step to extract the amide compound (II) with an organic solvent, where necessary.

In the amide extracting step (iv) in the embodiment shown in FIG. 3, a reaction mixture containing an amide compound produced in the hydration step (i) is supplied from a hydration reaction mixture supply line 22 to an extractor, and is extracted with an organic solvent supplied through an organic solvent supply line 32. As the organic solvent, an organic solvent contained in an organic layer (phase) obtained in the under-mentioned water layer separating step (v) can be employed. The obtained organic layer containing the amide compound is supplied from an amide mixture supply line 23 to the hydrolysis step (ii), and the water layer is recycled through a water recycle line 31 to the hydration step (i).

As examples of the organic solvent, there may be mentioned conventional hydrophobic organic solvents such as alcohols, ketones, aldehydes, esters, ethers, hydrocarbons, halogenated hydrocarbons and the like.

The alcohol includes, for instance, aliphatic alcohols each having 4 or more carbon atoms, alicyclic alcohols each having 4 or more carbon atoms, and aromatic alcohols each having 7 or more carbon atoms. As the aliphatic alcohol having 4 or more carbon atoms, there may be mentioned for example aliphatic alcohols each having about 4 to 12 carbon atoms (preferably about 4 to 9 carbon atoms), such as 1-butanol, 2-butanol, isobutyl alcohol and other $C_4$ alcohols; 1-pentanol, isoamyl alcohol, tert-amyl alcohol, 2-pentanol and other $C_5$ alcohols; 1-hexanol, 2-methyl-1-pentanol, 3-methyl-1-pentanol, 2,2-dimethyl-1-butanol, 2-ethyl-1-butanol, 4-ethyl-1-pentanol, 2-hexanol, 3-hexanol, 3-methyl-2-pentanol, 2,3-dimethyl-2-butanol, 2-methyl-3-pentanol, 3-methyl-3-pentanol, 4-methyl-2-pentanol, 2-methyl-2-pentanol and other $C_6$ alcohols; n-heptyl alcohol, 2-methyl-1-hexyl alcohol, 3-methyl-1-hexyl alcohol, 4-methyl-1-hexyl alcohol, 5-methyl-1-hexyl alcohol, 2-ethyl-1-pentanol, 3-ethyl-1-pentanol, 2,2-dimethyl-1pentanol, 3,3-dimethyl-1-pentanol, 4,4-dimethyl-1-pentanol, 2,3-dimethyl-1-pentanol, 2,4-dimethyl-1-pentanol, 3,4-dimethyl-1-pentanol and other $C_7$ alcohols; 1-octanol, 2-methyl-1-heptanol, 3-methyl-1-heptanol, 4-methyl-1-heptanol, 5-methyl-1-heptanol, 2-octanol, 3-octanol, 4-octanol, 2-methyl-2-heptanol, 3-methyl-2-heptanol, 4-methyl-2-heptanol, 5-methyl-2-heptanol, 6-methyl-2-heptanol, 2-methyl-3-heptanol, 3-methyl-3-heptanol and other $C_8$ alcohols; and 1-nonanol and other $C_9$ alcohols.

Examples of the alicyclic alcohol having 4 or more carbon atoms include cyclopentanol, cyclohexanol and other alicyclic alcohols each having about 4 to 12 carbon atoms. The aromatic alcohol having 7 or more carbon atoms includes, for instance, benzyl alcohol and other aromatic alcohols each having about 7 to 12 carbon atoms.

As the ketone, there may be exemplified with methyl ethyl ketone, diethyl ketone, methyl propyl ketone, methyl isopropyl ketone, methyl butyl ketone, methyl 1-methylpropyl ketone, methyl 2-methylpropyl ketone, ethyl propyl ketone and other ketones each having 4 or more carbon atoms (e.g. about 4 to 12 carbon atoms, and preferably about 4 to 9 carbon atoms).

The aldehyde includes, for example, butyraldehyde, valeraldehyde, benzaldehyde and other aldehydes each having 4 or more carbon atoms (e.g. about 4 to 12 carbon atoms, and preferably about 4 to 9 carbon atoms).

Examples of the ester include, ethyl acetate, propyl acetate, isopropyl acetate, butyl acetate, pentyl acetate, methyl propionate, ethyl propionate, ethyl butyrate, ethyl valerate and other esters each having 2 or more carbon atoms (e.g. about 2 to 12 carbon atoms, preferably about 2 to 9 carbon atoms).

As the ether, there may be mentioned ethyl ether, propyl ether, isopropyl ether, butyl ether, isobutyl ether and other ethers each having 4 or more carbon atoms (e.g. about 4 to 12 carbon atoms, preferably about 2 to 9 carbon atoms), for instance.

The hydrocarbon include, for example, pentane, hexane, heptane, octane and other aliphatic hydrocarbons; cyclopentane, cyclohexane and other alicyclic hydrocarbons; and benzene, toluene, xylene, ethylbenzene and other aromatic hydrocarbons. Examples of the halogenated hydrocarbon include methylene chloride, chloroform, carbon tetrachloride, dichloroethylene, chlorobenzene and so on.

These organic solvents can be used singly or in combination.

Preferred example of the organic solvent includes alcohols, ketones, aldehydes, esters, ethers and the like, and alcohols or ketones each having 4 or more carbon atoms (e.g. about 4 to 12 carbon atoms) are more desirable.

As the organic solvent used for extraction, use can also be made of an organic solvent obtained in the below-mentioned carboxylic acid recovering step (viii) or an unused (unrecycled) organic solvent in addition to, or in lieu of the organic solvent obtained in the water layer separating step (v).

The extraction may be effected in a conventional manner, such as by adding an organic solvent to a reaction mixture obtained in the above-mentioned hydration step, and mixing or shaking the resultant mixture, typically speaking. The extraction can be conducted in whichever system of batch system or continuous system. When the reaction mixture contains the manganese oxide which is a catalytic component, it is preferable to previously separate and recover the manganese oxide by, for example, filtration. The recovered manganese oxide can be reutilized in the hydration step.

An organic layer (phase) obtainable in the amide extracting step (v) is, as such or as suitably adjusted in terms of the concentration, supplied to a hydrolysis step (ii). Even when the amide compound is supplied to the hydrolysis step (ii) together with the organic solvent, a salt of a carboxylic acid produced by hydrolysis passes into a water layer so that the organic solvent can easily be separated from the salt of a carboxylic acid. Further, hydrolysis in the presence of an organic solvent practically results in smooth proceeding of the reaction and hence in a production of the salt of a carboxylic acid with a high yield. Accordingly, the organic solvent and the amide compound may be supplied to the hydrolysis step (ii) together with each other without separation, while the amide compound may also be separated from the organic layer to supply to the hydrolysis step (ii).

A water layer (phase) obtainable in the amide extracting step (iv) can be reutilized by recovering the same to the hydration step (i). Further, it is possible to recycle this water layer to the below-mentioned hydrolysis step (ii) or electrodialysis step (iii). The water layer can also be discharged, and even if the water layer is discharged, it does not contain by-products such as ammonium hydrogensulfate, being different from a process using sulfuric acid as a catalyst. Therefore, it does not cause environment destruction.

The reaction mixture obtainable in the hydration step (i) may be supplied to the hydrolysis step (ii) without subjecting to the amide extracting step (iv).

Hydrolysis step

In the hydrolysis step, the amide compound (II) formed in the hydration step is hydrolyzed in the presence of a base B to produce a corresponding salt (III) of a carboxylic acid and the base, and ammonia. Since a base is used as a hydrolyzing catalyst, the nitrogen atom of the amide compound, and in its turn, the nitrogen atom of the nitrile compound can be recovered as ammonia. Such advantages can clearly be differentiated from a process employing sulfuric acid as a catalyst.

In the hydrolysis step (ii) of the embodiment as illustrated in FIG. 3, an amide compound from an amide mixture supply line 23, and a base and water from a base-water supply line 42 are respectively supplied to a reactor to conduct hydrolysis reaction.

The base may be whichever of an inorganic base or organic base. As such inorganic base, there may be mentioned for example lithium hydroxide, sodium hydroxide, potassium hydroxide, rubidium hydroxide, caesium hydroxide and other alkali metal hydroxides; sodium carbonate, potassium carbonate and other alkali metal carbonates; sodium hydrogencarbonate, potassium hydrogencarbonate and other alkali metal hydrogencarbonates; magnesium hydroxide, calcium hydroxide and other alkaline earth metal hydroxides; and magnesium carbonate, calcium carbonate and other alkaline earth metal carbonates.

Examples of the organic base include triethylamine, tripropylamine, tributylamine and other mono-, di- or trialkylamines; piperazine, piperidine, N-methylpiperidine, morpholine and other cyclic amines; ethanolamine, triethanolamine and other alkanolamines; pyridine and other basic nitrogen-containing heterocyclic compounds. The base may preferably be a water-soluble base, because the electrodialysis step (iii) is carried out in the presence of water wherein a salt of a carboxylic acid produced in the hydrolysis step (ii) is separated into a carboxylic acid and a base.

Preferred base includes, for instance, alkali metal hydroxides (e.g. sodium hydroxide, potassium hydroxide, etc.) and alkali metal carbonates (e.g. sodium carbonate, potassium carbonate, etc.). Among them, sodium hydroxide, potassium hydroxide and the like can advantageously be used as the base.

Such bases may be employed independently or in combination. For enhancing the reaction rate, the pKa value of the base may for example be not less than 6 (e.g. about 6 to 30), preferably not less than 9 (e.g. about 9 to 20) and more preferably about 14 to 18.

The proportion of the base is, for example, not less than 0.5 gram equivalent, preferably about 1 to 5 gram equivalents and more preferably about 1.02 to 2 gram equivalents per mole of the amide compound. When the proportion of the base is less than 0.5 gram equivalent, it is liable that unreacted amide compound remains in large quantity and hence complicated operations such as a recovering operation are required. In contrast, the use of the base in an amount exceeding 5 gram equivalents is apt to cause economical disadvantages.

The concentration of the base in the reaction system is, for example, not less than 0.1N (normal) (e.g. about 0.1 to 5N), and preferably about 0.2 to 3N (e.g. about 0.5 to 3N). When the concentration of the base is less than 0.1N, not only the reaction rate is decreased but also a reaction volume required for obtaining a certain amount of a carboxylic acid is increased so that the productivity is apt to be sacrificed.

In the hydrolysis step (ii), water is usually used in an excess amount relative to the amide compound, and the amount of the water is, for instance, not less than 1 mole (e.g. about 1 to 500 moles) and preferably about not less than 1.5 mole (e.g. about 1.5 to 300 moles), relative to 1 mole of the amide compound.

The reaction may generally be conducted at 20° to 150° C., and preferably at 30° to 120° C. If the reaction is effected at a temperature of lower than 20° C., the reaction time is liable to be prolonged, and when the reaction temperature exceeds 150° C., a side reaction is occasionally proceeded and hence the yield is decreased. The reaction pressure may only be a pressure by which the reaction system is kept in a liquid phase at a reaction temperature, and is for example about 1 to 20 atm and preferably about 1 to 10 atm. The reaction may practically be effected at atmospheric pressure. The reaction time is not exemplified in a word since it depends on the species or amount of the base to be used, the reaction temperature and other reaction conditions, and the reaction may generally be conducted for about 0.1 to 10 hours. The reaction can be effected in either of batch system or continuous system.

A base and water recovered in the below-described electrodialysis step (iii) and/or carboxylic acid extracting step can efficiently be reutilized as the base and water to be used in the hydrolysis reaction. Further, it is also possible to devote or appropriate an unused base or water to the whole or a part of the required amount of the base or water to be used in the reaction.

Water layer separating step

A reaction mixture obtainable in the hydrolysis step is, when necessary, subjected to a water layer separating step. Separation of the water layer may be conducted by, for example, a method which comprises separating the reaction mixture obtained in the hydrolyzing step into an organic layer (organic phase) and a water layer (water phase). This step is useful when the reaction mixture obtained in the hydrolysis step contains an organic solvent. By way of an example, when the amide compound is supplied to the hydrolysis step together with an organic solvent used as an extractant in the amide extracting step, the reaction mixture obtainable in the hydrolysis step contains the organic solvent. Such organic solvent can easily and readily be recovered in the water layer separating step.

In the embodiment shown in FIG. 3, a reaction mixture produced in the hydrolysis step (ii) is supplied to a separator (separating apparatus) through a hydrolysis reaction mixture supply line 24 to separate the same into an organic layer containing an organic solvent, and a water layer containing a salt of a carboxylic acid and ammonia.

The organic layer contains the organic solvent as a main component so as to be reutilized, through the organic solvent supply line 32, as an extractant in the amide extracting step (iv). The organic layer can also be used as an extractant in the below-mentioned carboxylic acid extracting step (vii). On the other hand, the water layer is supplied via a carboxylate mixture supply line 25 to an ammonia recovering line (vi).

Incidentally, the reaction mixture obtainable in the hydrolysis step (ii) may be supplied, without being subjected to the water layer separating step (v), to the ammonia recovering step (v) or electrodialysis step (iii).

Ammonia recovering step

The water layer obtainable in the above water layer separating step is subjected to an ammonia recovering step, as necessary, to recover ammonia from the water layer. The recovery of ammonia can be carried out by, for instance, a process of stripping with the use of an inert gas, a process of vaporizing a dissolved ammonia by heating or other techniques.

In the ammonia recovering step (iv) of the embodiment illustrated in FIG. 3, ammonia dissolved in a water layer of the water layer separating step (v) which is supplied through the carboxylate mixture supply line 25 is stripped using an inert gas supplied from an inert gas supply line 34, and ammonia is recovered as a gaseous mixture containing the inert gas and ammonia via an ammonia recovering line 35. The inert gas includes, for example, nitrogen, helium, argon, methane, carbon dioxide, carbon monoxide and so forth. The recovery of ammonia may be effected by any manner such as a batch system or continuous system.

The recovered ammonia can be utilized as a raw material (reactant) for production of a cyano compound such as hydrogen cyanide, where such cyano compound is used as a raw material (reactant) for the nitrile compound. In other words, the ammonia can be reutilized as a nitrogen source for production of the nitrile compound. By way of illustration, hydrogen cyanide can be prepared from ammonia, methanol and carbon monoxide according to the following scheme (c).

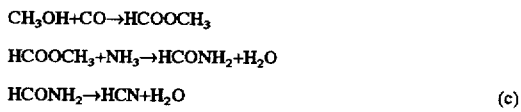

The hydrogen cyanide may also be prepared from ammonia, methane and oxygen according to the following scheme (d).

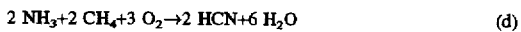

A nitrite compound (I) can readily be prepared by allowing the hydrogen cyanide to react with other material compound A (e.g. a ketone, an aldehyde, an epoxy (epoxide).

When ammonia is stripped with the use of methane as an inert gas in the ammonia recovering step (vi), an obtained gaseous mixture containing methane and ammonia can be supplied to the production process of hydrogen cyanide shown by the scheme (d). Therefore, ammonia can be reutilized or recycled with a high efficiency in a simple and easy manner.

The water layer separating step (v) and the ammonia recovering step (vi) may also be effected in the reverse order. Namely, it is possible that the reaction mixture obtained in the hydrolysis step (ii) is supplied to the ammonia recovering step (vi) to recover ammonia by stripping or other technique, and a resultant mixture containing a salt of a carboxylic acid, from which ammonia has been recovered, is supplied to the water layer separating step (v) to separate an organic layer containing an organic solvent from a water layer containing the salt of carboxylic acid. In such a case, the organic layer can be recycled to the amide extracting step (iv) or other steps, and the water layer can be supplied to the electrodialysis step (iii).

Further, ammonia formed in the hydrolysis step (ii) may not necessarily be recovered, and the reaction mixture in the hydrolysis step may be supplied to the electrodialysis step (iii), if necessary after subjected to the water layer separating step (v).

Electrodialysis step

In the electrodialysis step, a salt (III) of a carboxylic acid formed in the above hydrolysis step is subjected to electrodialysis to form a corresponding carboxylic acid (IV) and a base B.

Incidentally, with respect to the mechanism, apparatus, reaction conditions and others of the electrodialysis, the description in the explanation of the processes (A) and (B) can be referred to.

The concentration of a salt of a carboxylic acid in the electrodialysis may be selected from a range not adversely affecting the electrodialysis, and usually is about 0.1 to 5 normal. The electrodialysis can be effected in whichever of a batch system or continuous system.

According to the embodiment illustrated in FIG. 3, electrodialysis is conducted in the electrodialysis step (iii) in such a manner that a mixture containing a salt of carboxylic acid (III) and water produced in the hydrolysis step (ii) through a carboxylate mixture supply line 26, and water through a water supply line 40 to an electrodialyser equipped with an ion exchange membrane or others.

By effecting the electrodialysis step (iii), a corresponding carboxylic acid and base are formed from the carboxylic acid salt, and thus separated into a mixture containing the carboxylic acid and water, and a mixture containing the base and water. The formed mixture containing the carboxylic acid and water is, through a carboxylic acid mixture recycling line 38, mixed with a mixture of the carboxylic acid and water in the carboxylate mixture supply line 26 to be recycled to the electrodialysis step (iii). The mixture containing the carboxylic acid and water may occasionally contain an undecomposed salt of carboxylic acid according to a condition of the electrodialysis.

The mixture containing the base and water obtained in the electrodialysis step can be recovered from a base-water recovering line 33. The recovered base can be reutilized as a catalyst by recycling the same to the hydrolysis step (ii).

A part of a feeding mixture (a mixture from the carboxylate mixture supply line 26 and the carboxylic acid mixture recycling line 38) is supplied through a carboxylic acid mixture supply line 27 to a carboxylic acid extracting step (vii). The mixture containing the carboxylic acid and water formed in the electrodialysis step (iii) may be supplied directly to the carboxylic acid extracting step (vii) without recycling to the electrodialysis step (iii).

Carboxylic acid extracting step and carboxylic acid recovering step

A carboxylic acid formed in the electrodialysis step can be recovered by, where necessary, subjecting to a carboxylic acid extracting step and then to a carboxylic acid recovering step.

In the carboxylic acid extracting step (vii) of the illustrated embodiment of FIG. 3, a mixture containing a carboxylic acid and water formed in the electrodialysis step (iii) is supplied through the carboxylic acid mixture supply line 27 to an extractor, and the carboxylic acid is extracted with an organic solvent supplied from an organic solvent supply line 37.

As the organic solvent, there may be mentioned such organic solvents as described in the explanation of the amide extracting step (vi), such as alcohols, ketones, aldehydes, esters and ethers. Preferred examples of the organic solvent include alcohols and ketones each having 4 or more carbon atoms (e.g. about 4 to 12 carbon atoms). The extraction may be carried out in a conventional manner.

The organic layer containing the carboxylic acid and the organic solvent is supplied via a carboxylic acid extract supply line 28 to the carboxylic acid recovering step (viii). On the other hand, the water layer is withdrawn from a water recovering line 36 and hence can be recycled, together with a base-water mixture containing a base of the base-water recovering line 33, through a water supply line 41 to the electrodialysis step (iii), and, through the base-water supply line 42 to the hydrolysis step (ii).

In the carboxylic acid recovering step (viii), an organic layer containing a carboxylic acid and an organic solvent obtained in the above carboxylic acid extracting step (vii) is separated into the carboxylic acid and the organic solvent by distillation. The carboxylic acid is recovered from a carboxylic acid recovering line 29, and the organic solvent is recycled through the organic solvent supply line 37 to the carboxylic acid extracting step (vii) and hence is reutilizable as an extractant. The recovered organic solvent may also be employed as an extractant to be used in the amide extracting step (iv).

The recovery and extraction of the carboxylic acid may respectively be effected by any manner such as a batch system or continuous system.

The carboxylic acid formed in the electrodialysis step (iii) can also be separated and recovered by a conventional separating technique effected to a mixture containing a carboxylic acid and water, such as extraction, distillation, crystallization, recrystallization, column chromatography or a suitable combination of these techniques.

According to the processes (A) and (B) of the present invention, a salt of a catalytic component by-produced in a hydrolysis step of a nitrile compound or an amide compound is decomposed to regenerate a catalyst or ammonia and hence such catalyst or ammonia can be reutilized or recycled to a production process of a carboxylic acid. Therefore, a carboxylic acid can effectively be produced, including recovery of the catalytic component or other component, at a comparatively low cost with utilizing by-products. Further, the catalytic component (an acidic catalyst or a basic catalyst) and ammonia (or aqueous ammonia) can be formed with high efficiency in a simple and easy manner to be practically utilized in the production of a carboxylic acid. Moreover, the processes insure reutilization of the catalytic component and ammonia (or aqueous ammonia) with a high efficiency and hence they are highly useful for general purpose as a production process of a carboxylic acid.

The process (C) of the present invention, in which hydration of a nitrile compound using a manganese oxide catalyst, hydrolysis of the produced amide compound with the use of a basic catalyst, and electrodialysis of a salt of a carboxylic acid are effected in combination, does not produce such by-products as ammonium hydrogensulfate. Further, the process provides recovery of useful ammonia or catalyst in a simple and easy manner. Moreover, it insures effective utilization of the ammonia and the catalytic component.

The following examples are intended to illustrate the present invention in more detail, but should by no means limit the scope of the invention.

EXAMPLES

Example 1

1. Production step of isobutyronitrile

To a stainless steel tubular reactor (1 inch in diameter) charged with a zirconium catalyst were fed 0.5 mole/hr. of isobutyraldehyde and 1 mole/hr. of ammonia at an atmospheric pressure at 200° C. The produced gas was cooled to give a condensate, and the condensate was subjected to distillation to provide isobutyronitrile at a rate of 0.49 mole/hr.

2. Production step of sodium isobutyrate

In a 1-liter glass agitator, were heated 0.49 mole/hr. of isobutyronitrile and 270 ml/hr. of a 2N aqueous solution of sodium hydroxide at 80° C. to give ammonia gas. Further, the ammonia dissolved in the reaction mixture was stripped by bubbling a nitrogen gas into the reaction mixture. The ammonia gas formed in the agitator and the stripped gas were mixed and recycled to the production step of isobutyronitrile. As a result of analysis of the reaction mixture from which ammonia had been removed, sodium isobutyrate was formed at a rate of 0.49 mole/hr.

3. Electrodialysis step

In this step, was used an electrodialyser (type: TS2B-2-5, effective membrane area: 200 $cm^2 \times 5$ pairs, Tokuyama Co., Ltd., Japan) provided with a bipolar membrane (Neosepta® BP-1, Tokuyama Co., Ltd., Japan) and a cation exchange membrane (Neosepta® AMH, Tokuyama Co., Ltd., Japan), as illustrated in FIG. 1.

To an acid-base mixing chamber and an alkali chamber of the electrodialyser were recycled 5 liters of the reaction mixture obtained in the production process of sodium isobutyrate and 5 liters of a 0.4% aqueous solution of sodium hydroxide, respectively. By the same token, to an anion chamber and cation chamber of the electrodialyser were recycled each 5 liters of a 10% aqueous solution of sodium hydroxide, respectively. Thus, electrodialysis was effected at about 40° C. and at a current of 20 A (current density 10 A/100 $cm^2$) for 4 hours. As a result, 99% of the sodium isobutyrate was converted to isobutyric acid to give a 20% aqueous solution of isobutyric acid and a 2N aqueous solution of sodium hydroxide. The produced 2N aqueous solution of sodium hydroxide was recycled to the production step of sodium isobutyrate. Further, isobutyric acid was recovered from the 20% aqueous solution of isobutyric acid by extraction (extractant: methyl ethyl ketone, amount of extractant: 5 liters).

Example 2

1. Production step of sodium lactate

By using a 500 ml-glass agitator, 70 g/hr. of lactamide and 330 g/hr. of a 12% aqueous solution of sodium hydroxide were heated up to 80° C. to give ammonia gas. Further, the reaction mixture was allowed to contact with nitrogen gas by means of bubbling in the same manner as Example 1 to strip ammonia dissolved in the reaction mixture. The ammonia gas produced in the glass agitator was mixed with the stripped gas and the resulting mixture was recycled to a production step of lactamide. The reaction mixture from which ammonia had been removed contained 22% of sodium lactate, as a result of an analysis.

2. Electrodialysis step

To an acid-base mixing chamber and an alkali chamber of the electrodialyser as used in Example 1 were circulated 5 liters of the reaction mixture obtained in the production process of sodium isobutyrate and 5 liters of 0.4% aqueous solution of sodium hydroxide, and to an anion chamber and cation chamber were recycled 5 liters of 10% aqueous solution of sodium hydroxide, respectively. Thus, electrodialysis was carried out at a current of 20 A for 4 hours. Resultantly, 99% of the sodium lactate was converted to lactic acid, and a 20% aqueous solution of lactic acid and a 12% aqueous solution of sodium hydroxide were obtained. The 12% aqueous solution of sodium hydroxide was then recycled to a production step of sodium lactate. Further, lactate was recovered from the 20% aqueous solution of lactic acid by means of concentration.

Example 3

According to the production scheme (flow chart) illustrated in FIG. 3, 2-hydroxy-4-methylthiobutanoic acid was prepared.

(1) Hydration step [step (i)]

A manganese dioxide of δ-structure was pulverized and comminuted (graded) to give a particle size of 10 to 20 mesh. A glass tubular reactor (inner diameter 4 cm, length 60 cm) equipped with a Jacket was charged with 600 cc (350 g) of the comminuted manganese dioxide, and a warm water at 50° C. was flowed into the jacket.

To the tubular reactor were supplied 2-hydroxy-4-methylthiobutanenitrile (2-hydroxy-4-methylthiobutyronitrile), which had been prepared from acrolein, methyl mercaptan and prussic acid (hydrogen cyanide), from a nitrite supply line 21 at a rate of 131 g per hour, and water from a water supply line 39 (unused water) and a water recycle line 31 (a recycled water from the step (iv)) at a total flow rate of 740 g per hour. As a result, the conversion rate of the supplied 2-hydroxy-4-methylthiobutanenitrile to 2-hydroxy-4-methylthiobutanamide (2-hydroxy-4-methylthiobutyramide) was 100%. The 2-hydroxy-4-methylthiobutanamide was formed at a rate of 149 g per hour.

(2) Amide extracting step [step (iv)]

To a 300 ml-inner capacity glass tube (extractor) charged with Raschig rings were supplied continuously the reaction mixture obtained in the above hydration step via a hydration reaction mixture supply line 22, and an extractant containing methyl ethyl ketone and a small amount of dissolved water (an organic layer of the step (v)) from an organic solvent supply line 32 at a flow rate of 690 g per hour (620 g per hour in terms of methyl ethyl ketone).

Resultantly, an organic layer containing 2-hydroxy-4-methylthiobutanamide and a small amount of water and a water layer containing a small amount of methyl ethyl ketone were obtained respectively at flow rates of 838 g per hour (149 g/hr. in terms of 2-hydroxy-4-methylthiobutanamide) and 890 g per hour. After distilling off the methyl ethyl ketone, the water layer was recycled through a water recycling line 31 to the hydration step (i).

(3) Hydrolysis step [step (ii)]

To 1-liter capacity glass reactor equipped with a stirrer were supplied the organic layer obtained in the amide extracting step (iv) through an amide mixture supply line 23 continuously, and 8% aqueous solution of sodium hydroxide containing a small quantity of sodium 2-hydroxy-4-methylthiobutanoate (a mixture of an aqueous solution obtained in the step (iii) and a water layer of the step (vii)) through a base-water supply line 42 at a flow rate of 540 g per hour, and the hydrolysis reaction was carried out at a reaction temperature of 60° C.

Resultantly, a reaction mixture containing sodium 2-hydroxy-4-methylthiobutanoate (230 g/hr.), ammonia (17 g/hr.), water and methyl ethyl ketone was obtained at a flow rate of 1,390 g per hour.

(4) Water layer separating step [step (v)]

A reaction mixture obtained in the hydrolysis step (ii) was supplied through a hydrolysis reaction mixture supply line 24 to a separator for separation. The separated organic layer (a mixture of methyl ethyl ketone mixture and 10% of water) was recycled through the organic solvent supply line 32 to the amide extracting step at a flow rate of 690 g per hour, as described above.

(5) Ammonia recovering step [step (vi)]

To an ammonia diffusing column (tower) packed with Raschig rings were supplied a water layer containing sodium 2-hydroxy-4-methylthiobutanoate obtained in the water separating step (v), and ammonia, from a carboxylate mixture supply line 25, and methane gas via an inert gas supply line 34 connected to the bottom of the ammonia diffusing column at a flow rate of 23 liters per hour.

A methane-ammonia gas mixture was obtained from the top of the ammonia diffusing column. This gaseous mixture was supplied to a hydrogen cyanide preparing step from an ammonia recycling line 35.

(6) Electrodialysis step [step (iii)]

In this step, an electrodialyser (type: TS2B-2-5; effective area 200 $cm^2 \times 5$ pairs, Tokuyama Co., Ltd., Japan) composed of a bipolar membrane and a cation exchange membrane (respectively manufactured by Tokuyama Co., Ltd., Japan) was used as an electrodialyser.

An aqueous solution of sodium 2-hydroxy-4-methylthiobutanoate (carboxylate mixture supply line 26) from which ammonia had been eliminated in the ammonia recovering step (vi) was mixed with an aqueous solution (carboxylic acid mixture recycling line 38) containing 2-hydroxy-4-methylthiobutanoic acid and undecomposed sodium 2-hydroxy-4-methylthiobutanoate obtained in the electrodialysis, and the resultant mixture was supplied to the electrodialyser. The concentration of sodium 2-hydroxy-4-methylthiobutanoate in this mixture was 8.8% by weight and the feeding amount of the mixture to the electrodialyser was 3,600 g per hour. While, a part of the mixture (655 g per hour) was supplied to a carboxylic acid extracting step (vii) from a carboxylic acid mixture supply line 27.

An aqueous solution of sodium hydroxide obtained in the electrodialysis was mixed, through a base-water recovering line 33, with a water layer (an aqueous solution containing undecomposed sodium 2-hydroxy-4-methylthiobutanoate: a water recovering line 36) of the below-mentioned carboxylic acid extracting step (vii), and a part of the resultant mixture was supplied as an electrolyte through a water supply line 41 to the electrodialyser, and the most of the remained was recycled or recycled to the hydrolysis step (ii). Further, water (new water) was supplied from a water supply line 40 to the electrodialyser at a rate of 18 g per hour.

23

(7) Carboxylic acid extracting step [step (vii)]

To a diffusing column was supplied a mixture (an aqueous solution containing 2-hydroxy-4-methylthiobutanoic acid and undecomposed sodium 2-hydroxy-4-methylthiobutanoate) of a solution containing a carboxylic acid salt of the carboxylate mixture supply line 26 and a solution containing a carboxylic acid of the carboxylic acid mixture recycling line 38 through the carboxylic acid mixture supply line 27, and was fed methyl ethyl ketone as an extractant from an organic solvent supply line 37 for extraction.

As a result of the extraction, an extract (organic layer) containing 18.5% by weight of 2-hydroxy-4-methylthiobutanoic acid, 73% by weight of methyl ethyl ketone and 8.5% by weight of water was obtained at a flow rate of 805 g per hour. A water layer containing undecomposed sodium 2-hydroxy-4-methylthiobutanoate was recycled to the hydrolysis step (ii) and the electrodialysis step (iii) together with the aqueous solution of sodium hydroxide of a base-water recovering line 33 through a water recovering line 36, as described above.

(8) Carboxylic acid recovering step [step (viii)]

The extract (organic layer) obtained in the carboxylic acid extracting step (vii) was supplied to a distillating column (distillation tower) for distillation. As a result, an aqueous solution containing 80% of 2-hydroxy-4-methylthiobutanoic acid and having Gardner color scale 4 was obtained at a flow rate of 178 g per hour through a carboxylic acid recovering line 29 from the bottom of the column. Further, methyl ethyl ketone distillated from the top of the column was recycled through the organic solvent supply line 37 to the carboxylic acid extracting step (vii) to reutilize as an extractant.

What is claimed is:

1. A process for producing a carboxylic acid which comprises:

(1) hydrolyzing a nitrile compound or an amide compound (a) in the presence of an acidic catalyst to form a carboxylic acid and an ammonium salt of the acidic catalyst, or (b) in the presence of a basic catalyst to form a salt of a carboxylic acid with the basic catalyst, and ammonia or aqueous ammonia, and (2a) electrodialysing the by-produced ammonium salt of the acidic catalyst to form an acid and ammonia or aqueous ammonia, or (2b) electrodialysing the produced salt of the carboxylic acid with the basic catalyst to form the corresponding carboxylic acid and the corresponding base.

2. The process for producing a carboxylic acid according to claim 1, wherein said process further comprises:

(A) a process comprising at least one step selected from (i) a step of reutilizing the produced acid as a catalyst to be used in the hydrolysis step of the nitrile compound or the amide compound, and (ii) a step of reutilizing the ammonia or aqueous ammonia produced in the step (2a) as a nitrogen source for the nitrile compound or the amide compound, (B) a process comprising at least one step selected from (i) a step of reutilizing the base produced in the step (2b) as a catalyst to be used in the hydrolysis step of the nitrile compound or the amide compound, and (ii) a step of reutilizing the ammonia or aqueous ammonia produced in the step (1)(b) as a nitrogen source for the nitrile compound or the amide compound, or (C) a process comprising (i) a hydration step of hydrating a nitrile compound in the presence of a manganese oxide to form a corresponding amide compound, (ii) a hydrolysis step of hydrolyzing the amide compound obtained in said hydration step in the presence of a base to form a corresponding salt of a carboxylic acid and ammonia, and (iii) an electrodialysis step of electrodialysing the salt of the carboxylic acid in an aqueous mixture obtained in said hydrolysis step to form the corresponding carboxylic acid and the corresponding base.

3. The process for producing a carboxylic acid according to claim 1, wherein (i) the acid or base formed by the electrodialysis is reutilized as a catalyst to be used in the hydrolysis step of the nitrile compound or the amide compound, and (ii) the ammonia or aqueous ammonia formed by the hydrolysis or electrodialysis is reutilized as a nitrogen source for the nitrile compound or the amide compound.

4. A process for producing a carboxylic acid according to claim 1, wherein the electrodialysis is carried out by using an ion exchange membrane comprising a bipolar membrane and at least one membrane selected from a cation exchange membrane and an anion exchange membrane.

5. A process for producing a carboxylic acid according to claim 1, wherein said nitrile compound is a cyanohydrin compound.

6. The process for producing a carboxylic acid according to claim 1, wherein said basic catalyst has a pKa value of not less than 6.

7. The process for producing a carboxylic acid according to claim 1, wherein said basic catalyst is a hydroxide of an alkali metal.

8. The process for producing a carboxylic acid of claim 1 which comprises:

(A) the steps of;
        hydrolyzing a nitrile compound or an amide compound in the presence of an inorganic acid as a catalyst,
        electrodialysing an ammonium salt of the inorganic acid by-produced in the hydrolysis step,
        recycling the inorganic acid obtained in the electrodialysis step to the hydrolysis step of the nitrile compound or the amide compound to be used as the catalyst, and
        recycling ammonia produced in the electrodialysis step as a nitrogen source for the nitrile compound or the amide compound, or (B) the steps of;
        hydrolyzing a nitrile compound or an amide compound in the presence of a hydroxide of an alkali metal as a catalyst,
        electrodialysing an alkali metal salt of a carboxylic acid produced in the hydrolysis step to form the carboxylic acid and a hydroxide of the alkali metal,
        recycling the hydroxide of the alkali metal obtained in said electrodialysis step to the hydrolysis step of the nitrile compound or the amide compound to be used as the catalyst, and
        recycling ammonia obtained in said electrodialysis step as a nitrogen source for the nitrile compound or the amide compound.

9. A process for producing a carboxylic acid according to claim 2, wherein the process (C) further comprises (iv) an amide extracting step of extracting a reaction mixture of the hydration step (i) containing said amide compound with an organic solvent and supplying the extracted organic layer containing said amide compound to the hydrolysis step (ii).

10. A process for producing a carboxylic acid according to claim 2, wherein said process (C) further comprises (vi)

an ammonia recycle step of recycling ammonia produced in the hydrolysis step (ii) as a nitrogen source for the nitrile compound of (C)(i).

11. A process for producing a carboxylic acid according to claim 10, wherein said recycle step comprises the steps of;
   stripping the ammonia with methane gas,
   forming hydrogen cyanide from the obtained gaseous mixture of ammonia and methane, and
   utilizing the obtained hydrogen cyanide as a reactant for the nitrile compound.

12. The process for producing a carboxylic acid as claimed in claim 2, wherein said process (C) further comprises:
   (vii) a carboxylic acid extracting step of extracting a mixture containing the carboxylic acid and water produced in the electrodialysis step (iii) with an organic solvent,
   a separating step of separating the carboxylic acid produced in said extracting step from the organic solvent, and
   a recycle step of recycling the organic solvent obtained in said separating step as an extractant to be used in said carboxylic acid extracting step or an amide extracting step.

13. A process for producing a carboxylic acid as claimed in claim 9 or 12, wherein at least one hydrophobic organic solvent selected from the group consisting of alcohols, ketones, aldehydes, esters and ethers is used as the organic solvent for extraction.

14. The method of producing a carboxylic acid according to claim 2, wherein said process (C) further comprises a step of reutilizing the base produced in the electrodialysis step (iii) as the base to be used in the hydrolysis step (ii).

15. The method of producing a carboxylic acid of claim 1 which comprises:
   (i) a hydration step of hydrating a cyanohydrin compound in the presence of a manganese oxide to form an aqueous mixture containing the corresponding hydroxyamide,
   (ii) a hydrolysis step of hydrolyzing the hydroxy-amide obtained in said hydration step (i) in the presence of an alkali metal hydroxide and water to form an alkali metal salt of a corresponding hydroxycarboxylic acid, and ammonia,
   (v) a separating step of separating a mixture containing the alkali metal salt of the hydroxycarboxylic acid and ammonia obtained in said hydrolysis step (ii) into ammonia and a water layer containing the alkali metal salt of the hydroxycarboxylic acid,
   (iii) an electrodialysis step of electrodialysing the water layer obtained in said separating step (v) by means of an electrodialyser comprising a bipolar membrane and at least one ion exchange membrane selected from a cation exchange membrane and an anion exchange membrane to form the hydroxycarboxylic acid and an alkali metal hydroxide,
   a recycling step of recycling the ammonia obtained in said separating step (v) to be used as a reactant for preparation of hydrogen cyanide, which is used as a reactant for the cyanohydrin compound, and
   a recycling step of recycling the alkali metal hydroxide obtained in the electrodialysis step (iii) to the hydrolysis step (ii).

16. A process for producing a carboxylic acid according to claim 15, wherein said process further comprises at least one step selected from the group consisting of:
   (iv) an amide extracting step of extracting a hydroxyamide from the aqueous reaction mixture obtained in the hydration step (i) with the use of an organic solvent,
   (vii) a carboxylic acid extracting step of extracting the hydroxycarboxylic acid with an organic solvent from a mixture containing the hydroxycarboxylic acid, the alkali metal hydroxide and water obtained in the electrodialysis step (iii), and
   (viii) a carboxylic acid recovering step of recovering the hydroxycarboxylic acid from an organic layer obtained in the carboxylic acid extracting step (vii).

17. A process for producing a carboxylic acid according to claim 15, wherein said cyanohydrin compound is a compound shown by the following formula

wherein $R^1$ and $R^2$ independently represent a hydrogen atom or a hydrocarbon group which may have a substituent, or $R^1$ and $R^2$ may form a ring together with the adjacent carbon atom, with a proviso that $R^1$ and $R^2$ are not concurrently hydrogen atoms.

18. A process for producing a carboxylic acid as claimed in claim 17, wherein said cyanohydrin compound is a compound of the formula (Ia) where $R^1$ and $R^2$ respectively represents a $C_{1-12}$ alkyl group, a $C_{2-12}$ alkenyl group, a $C_{2-12}$ alkynyl group, a $C_{3-10}$ cycloalkyl group, a $C_{6-14}$ aryl group or a $C_{7-10}$ aralkyl group.

19. A process for producing a carboxylic acid according to claim 17, wherein said cyanohydrin compound is 2-hydroxy-4-methylthiobutanenitrile.

20. A process for producing a carboxylic acid according to claim 16, wherein said process further comprises at least one step selected from the group consisting of:
   (ix) a recycling step of recycling a water layer obtained in the amide extracting step (iv) to hydrate the cyanohydrin in the hydration step (i),
   (x) a recycling step of separating a water layer obtained in the separating step (v) by a liquid separation and recycling the obtained organic layer to the amide extracting step (iv) to be used as the organic solvent,
   (xi) a recycling step of recycling the water layer obtained in the carboxylic acid extracting step (vii) to the hydrolysis step (ii) to be used as the water, and
   (xii) a recycling step of recovering an organic solvent from the organic layer obtained in the carboxylic acid extracting step (vii) and reutilizing the organic solvent as an extractant to be used in the carboxylic acid extracting step (vii) or the amide extracting step (iv).

* * * * *